(12) United States Patent
Castulik et al.

(10) Patent No.: US 8,884,009 B2
(45) Date of Patent: Nov. 11, 2014

(54) PROCESS FOR MAKING BORTEZOMIB AND INTERMEDIATES FOR THE PROCESS

(75) Inventors: Jakub Castulik, Blansko (CZ); Miroslav Zabadal, Blansko (CZ)

(73) Assignee: Synthon BV, Nijmegen (NL)

( * ) Notice: Subject to any disclaimer, the term of this patent is extended or adjusted under 35 U.S.C. 154(b) by 0 days.

(21) Appl. No.: 13/879,515

(22) PCT Filed: Oct. 14, 2010

(86) PCT No.: PCT/EP2010/065421
§ 371 (c)(1),
(2), (4) Date: Apr. 15, 2013

(87) PCT Pub. No.: WO2012/048745
PCT Pub. Date: Apr. 19, 2012

(65) Prior Publication Data
US 2013/0203988 A1    Aug. 8, 2013

(51) Int. Cl.
*C07D 241/24* (2006.01)
*C07F 9/6571* (2006.01)
*C07F 9/38* (2006.01)
*C07F 5/02* (2006.01)
*C07F 5/04* (2006.01)

(52) U.S. Cl.
CPC ........ *C07F 9/657163* (2013.01); *C07D 241/24* (2013.01); *C07F 9/3895* (2013.01); *C07F 5/025* (2013.01); *C07F 9/657181* (2013.01); *C07F 5/04* (2013.01)
USPC .......................................... 544/229; 544/406

(58) Field of Classification Search
CPC .............................. C07F 5/025; C07D 241/24
USPC ................................................. 544/229, 406
See application file for complete search history.

(56) References Cited

U.S. PATENT DOCUMENTS

| 5,780,454 A | 7/1998 | Adams et al. |
| 2006/0189806 A1 | 8/2006 | Bernardini et al. |

FOREIGN PATENT DOCUMENTS

| WO | WO 96/13266 | 5/1996 |
| WO | WO 02/059130 | 8/2002 |
| WO | WO 02/059131 | 8/2002 |
| WO | WO 2004/069805 | 8/2004 |
| WO | WO 2005/014604 | 2/2005 |
| WO | WO 2005/097809 | 10/2005 |
| WO | WO 2009/004350 | 1/2009 |
| WO | WO 2009/036281 | 3/2009 |

*Primary Examiner* — Brian McDowell
(74) *Attorney, Agent, or Firm* — Mark R. Buscher

(57) ABSTRACT

The invention relates to processes of making bortezomib of formula (1) enantiomers thereof and/or intermediates thereof, comprising at least one step of coupling a carboxylic acid with an amine, wherein the coupling step is performed in a presence of the compound of formula (8), wherein A is C1-C6 alkyl group, preferably wherein A is n-propyl group.

13 Claims, No Drawings

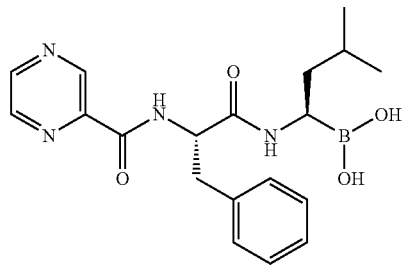

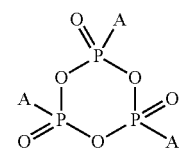

PROCESS FOR MAKING BORTEZOMIB AND INTERMEDIATES FOR THE PROCESS

BACKGROUND OF THE INVENTION

Bortezomib, chemically 3-methyl-1(R)-[N-(pyrazin-2-yl-carbonyl)-L-phenylalanyl-amino]-butylboronic acid of the formula (1)

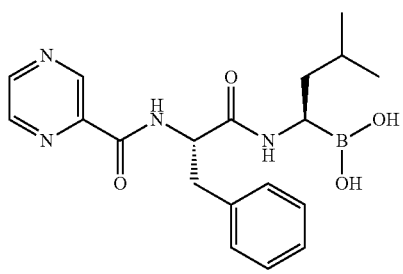

(1)

is a pharmaceutically active compound used in treatment various tumors. Bortezomib is a selective proteasome inhibitor Inhibition of proteasome by bortezomib prevents the degradation of intracellular proteins, affecting multiple signalling cascades within cells leading to cell death and tumor growth inhibition.

Structurally, bortezomib is a boronated dipeptidic compound comprising L-leucine and L-phenylalanine moieties. Therefore, it comprises two chiral carbons and the molecule has rigid spatial orientation thus being a single diastereomer. It may form acid addition salts.

In solid state, bortezomib is present in trimeric boroxine form. Various crystalline polymorphs of bortezomib have been described in the literature.

Pharmaceutical compositions currently in medical use and sold, e.g., under the trade name Velcade comprise a sterile lyophilized mixture of bortezomib with mannitol, which excipient also reacts with bortezomib during lyophilization process upon formation a mannitol boronic ester.

Bortezomib has been first disclosed in WO 96/13266. The mannitol esters of bortezomib have been disclosed in WO 2002/059130, the trimeric form of bortezomib has been disclosed in WO 2002/059131.

As bortezomib is a dipeptide compound consisting of pyrazin-2-yl carboxylic acid (A), L-phenylalanine (B) and (R)-1-amino-3-methylbutylboronic acid (C) moieties, its structure may be generally denoted as

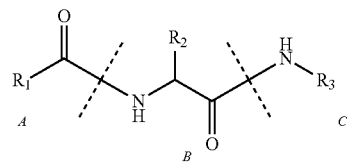

and its synthesis follows basic approaches in making peptides. Peptides are commonly prepared by coupling the acidic and aminic parts of corresponding amino acids using a coupling agent. In case of dipeptides, two possible routes shown below (approaches AB+C and A+BC, resp.) are principally applicable (necessary NH- or OH-protection excluded):

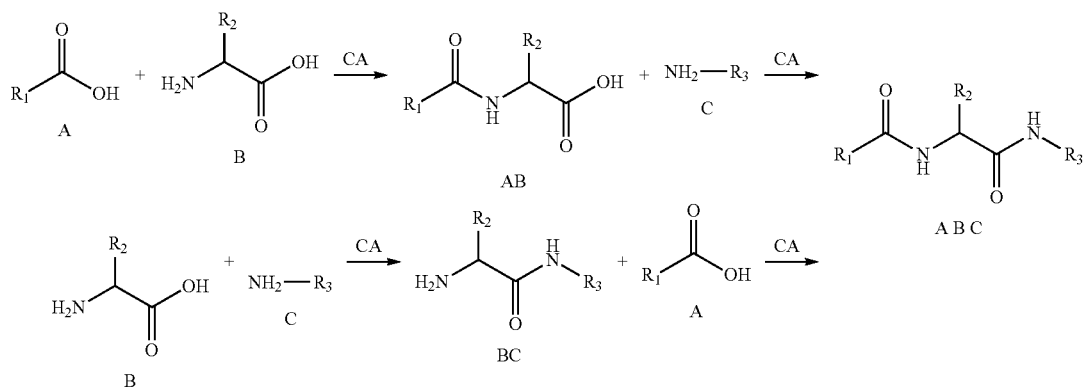

In each of four above steps indicated by an arrow, a coupling agent ("CA") is necessary for performing the peptide-forming reaction.

In the basic patent family (WO 96/13266, EP 788360, U.S. Pat. No. 5,780,454 and others), no process of making bortezomib (denoted there as MG-341) is explicitly exemplified. As follows from the description, bortezomib may be probably prepared using a procedure starting with coupling of (1R)—(S)-pinanediol-1-amino-3-methylbutane-1-boronate of formula (2) with appropriate N-protected (pref. with Boc group) phenylalanine compound of formula (3) (see the above A+BC approach and "Route I" in the Scheme 1 below). The originator has filed a later patent application WO 2005/097809 disclosing improvements of this basic route. This application is in fact the first specific disclosure of the Route I process.

Process according the Route II of the Scheme 1 below, i.e. that of converting the compound of formula (2) directly to a compound of formula (4) using a peptide synthon of formula (6) (see the above AB+C approach), has been disclosed in recent applications WO 2009/004350 (Pliva/Teva) and WO 2009/036281 (Dr. Reddy).

Both routes produce bortezomib via its B—OH protected precursor of formula (4). The OH-groups in the compound (4) are typically protected by a chiral (S)-pinanediol protective group and the removal of this group (by a transesterification reaction with 2-methylpropane-boronic acid in acidic environment, as disclosed in WO 2005/097809) represents the common last step in making bortezomib (1).

As indicated above, coupling agents are necessary for coupling carboxylic acids with amines in both basic routes leading to bortezomib. At present, classical coupling agents, such as TBTU ((O-benzotriazole-1-yl)-N,N,N',N'-tetramethyluronium tetrafluoroborate) and DCC (N,N'-dicyclohexylcarbodiimide) in combination with 1-hydroxybenztriazole, are used in the prior art processes for making bortezomib. Such coupling agents however exhibit many disadvantages in the coupling process and improvement in this respect is therefore desirable.

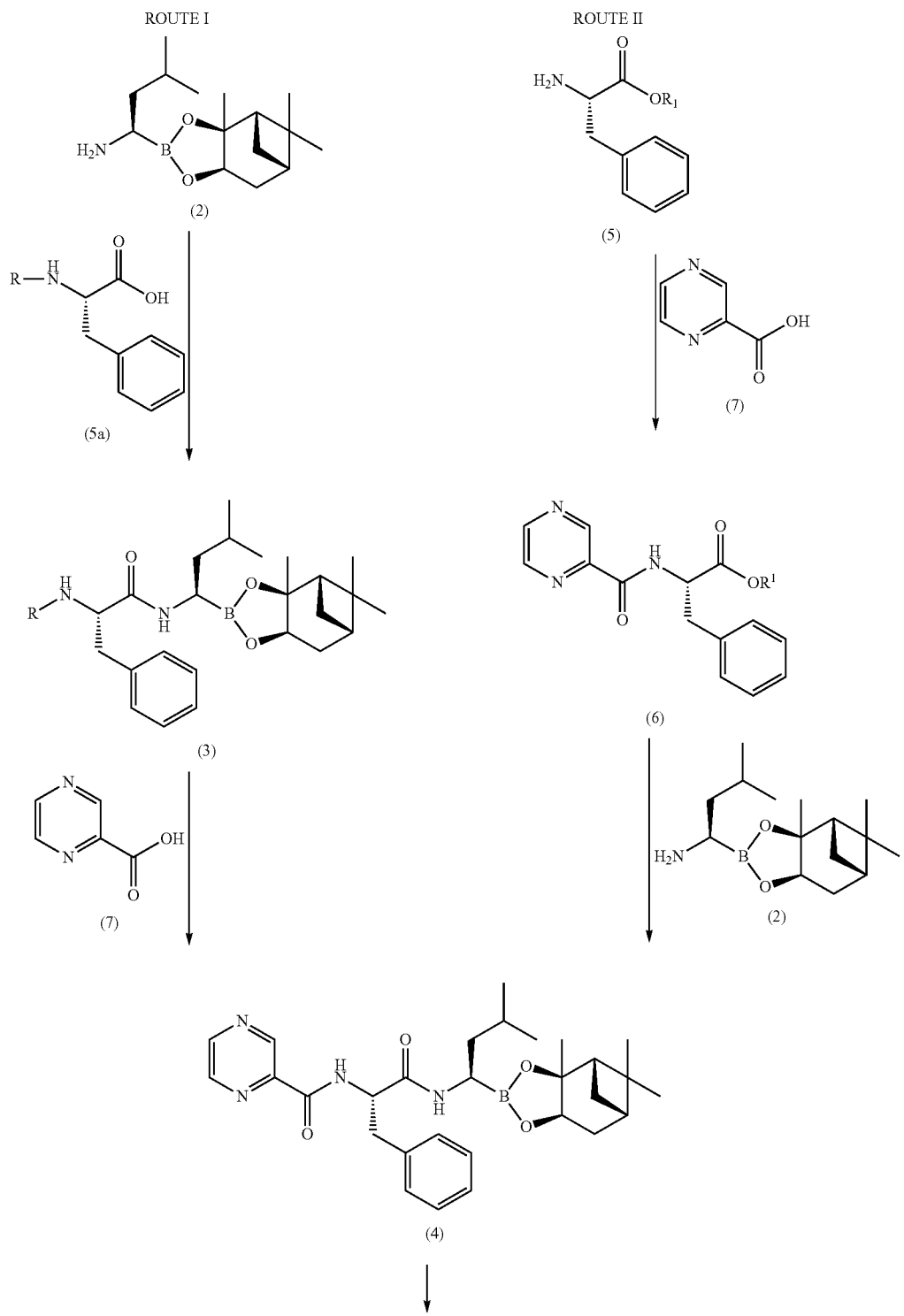

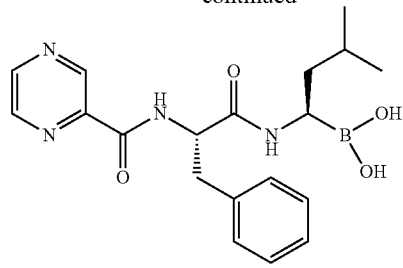

(1)

SUMMARY OF THE INVENTION

The present invention is based on the discovery of an improved process for making bortezomib characterized by using a specific coupling agent, which is cheaper, less toxic and more effective.

The first and most general aspect of the present invention deals with the use of cyclic alkyltriphosphonate anhydride of formula (8)

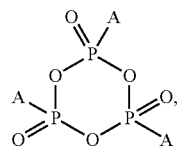

(8)

wherein A is C1-C6 alkyl group, preferably n-propyl group, as a coupling agent in processes for making bortezomib, its enantiomers and intermediates, particularly in processes for making a protected bortezomib intermediate of general formula (4A),

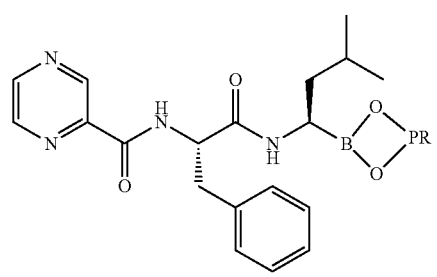

(4A)

wherein PR is a chiral protective group, preferably (S)-pinanediol protective group.

In the second aspect, the invention provides a process of coupling protected (R)-1-amino-3-methylbutylboronic acid of general formula (2A), particularly the compound of formula (2) and/or an acid addition salt thereof, preferably the trifluoroacetate salt,

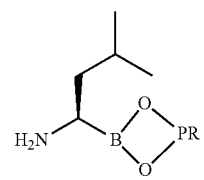

(2A)

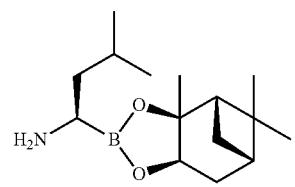

(2)

with a compound of formula (6)

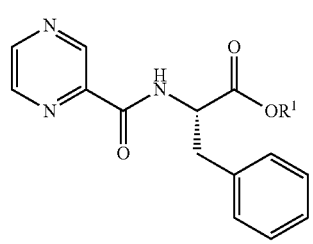

(6)

wherein R1 is hydrogen, upon formation of the compound of the formula (4A) above and preferably of formula (4)

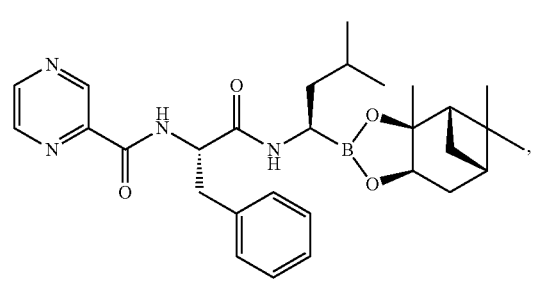

(4)

characterized in that the coupling reaction is performed in the presence of the compound of the formula (8) above, wherein A is C1-C6 alkyl group, preferably wherein A is n-propyl group.

In a specific aspect, the compound of the formula (6) above, wherein R1 is hydrogen, is prepared by a process, in which the compound of formula (5)

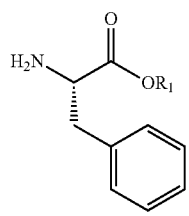

(5)

wherein R1 is a C1-C4 alkyl group and is preferably methyl group, is coupled with the compound of formula (7)

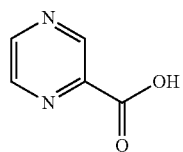

(7)

in a presence of the compound of the formula (8) above, and the so formed intermediate of formula (6), in which R1 is a C1-C4 alkyl group, is hydrolysed to yield a compound of formula (6), in which R1 is hydrogen.

In a third aspect, the invention provides a process of coupling protected 1-amino-3-methylbutylboronic acid of general formula (2A), particularly the compound of formula (2) and/or an acid addition salt thereof, preferably the trifluoroacetate salt, with a compound of formula (5a)

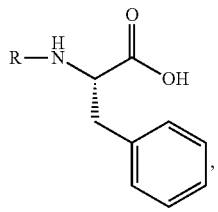

(5a)

wherein R is a N-protective group, preferably tert.butyloxycarbonyl group, upon formation of compound of general formula (3A) and particularly of formula (3)

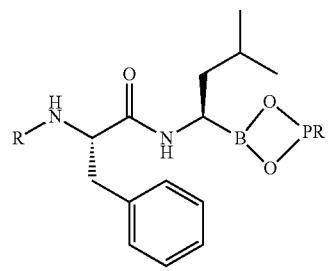

(3A)

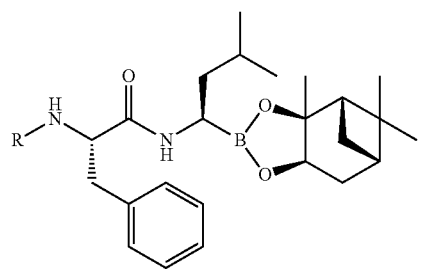

(3)

characterized in that the coupling reaction is performed in the presence of a compound of the formula (8) above, wherein A is C1-C6 alkyl group, preferably in which A is n-propyl group, followed by one or more steps of converting the compound of the above formula (3A), particularly of the above formula (3), to bortezomib.

In a specific aspect, the converting step comprises deprotection the N-protective group in the compound of the above defined formulas (3A) and/or (3) to provide a compound of formula (3A) and/or (3), in which R is hydrogen.

In a next aspect, the converting step further comprises coupling the compound of formula (3A) and/or (3), in which R is hydrogen, with a compound of the formula (7) above, characterised in that the coupling reaction proceeds in a presence of the compound of the formula (8) above.

DETAILED DESCRIPTION OF THE INVENTION

The present invention is focused on an improved process for making bortezomib of formula (1). More specifically, it is focused on making the penultimate intermediate of bortezomib of general formula (4A), which is characterised in that the future bortezomib boronic acid moiety is still protected by a B—OH protecting group of chiral structure and rigid conformation. The chiral structure of the protective group is preferred as bortezomib is a single enantiomer of a chiral compound with two stereogenic centres and it is advantageous to retain proper configuration on these centres during the synthesis. At presently known processes, the useful protective group is a chiral (S)-pinanediol group, thereby the penultimate bortezomib intermediate has the structure corresponding to the formula (4).

The processes of the present invention will be further illustrated and exemplified on compounds bearing the chiral (S)-pinanediol protective group, however they may be used, without limitation, for making also any other B—OH protected intermediates of bortezomib of a general formula (4A), wherein PR is a chiral protective group. Such chiral protective group essentially comprises a vicinal diol comprising at least one chiral carbon. In an example, the other chiral protective groups may be, e.g., chiral 1,2-dicyclohexylethane-1,2-diol (DICHED), chiral 1,2-diisopropylethane-1,2-diol (DIPED) etc., including those as disclosed in WO 2005/097809.

The processes of the present invention may be also used in making enantiomers of bortezomib, i.e. compounds of the same chemical formula but with different spatial orientation of atoms. The "enantiomers" also comprise mixtures of these enantiomers.

As bortezomib is a dipeptide compound consisting of three building blocks linked together by two peptidic bonds, there exist two possible synthetic routes varying by the order of building the blocks together. In particular, each of these two routes comprises two reaction steps, which may be characterised as coupling steps between a carboxyl-group and an amino-group upon forming an amido group. The reaction partners bearing the both reactive groups have rigid spatial orientation and the coupling product must maintain this orientation without racemisation or epimerization; therefore the coupling reaction must be performed under conditions, at which the racemisation/epimerization is minimized. In general, such coupling reaction between the acid and the amine must run in a presence of a suitable coupling agent. In the prior art documents dealing with bortezomib chemistry, various coupling agents were used, in particular TBTU ((O-benzotriazole-1-yl)-N,N,N',N'-tetramethyluronium tetrafluoroborate) and DCC (N,N'-dicyclohexylcarbodiimide), typically in combination with 1-hydroxybenztriazole.

The processes of the present invention are based on using a coupling agent of a general formula (8) wherein A is C1-C6 alkyl group. Preferably, A is n-propyl group and the coupling agent has thus a structure of the formula (8A).

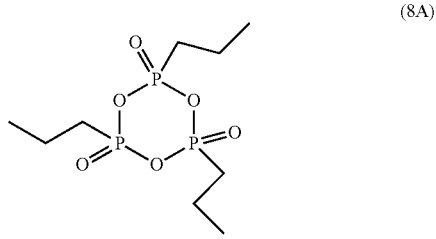

(8A)

The compound of formula (8) is a cyclic phosphonic acid anhydride which reacts with the water liberated during the amidation reaction upon forming a linear triphosphate:

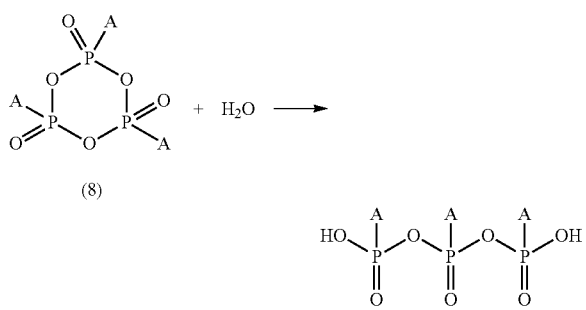

Both the cyclic and the linear triphosphates of the above scheme are well soluble in water and in various organic solvents and can thus be easily removed from the reaction product. They are non-toxic compounds, which may be handled by standard means. The amidation reaction proceeds generally at ambient and/or lower than ambient temperature, with almost a quantitative conversion.

The compounds of formula (8) have been disclosed, e.g., in WO 2005/014604.

Without limitation, the details and advantages of the present invention will be further explained on using tris-n-propyl cyclic triphosphonate anhydride (2,4,6-triprop-1-yl-1,3,5-trioxa-2,4,6-triphosphinane-2,4,6-trioxide) of formula (8A) [sometimes abbreviated herein as T3P] as the preferred coupling agent, as this compound is commercially available, e.g. under trade name Allesan CAP.

It was found out that the compound of formula (8A) has several remarkable advantages in comparison to other coupling reagents used in bortezomib chemistry:

1. It exhibits minimal rate of epimerization during coupling; configuration on stereogenic centres is maintained;

2. It has very low toxicity and low sensitization potential; both TBTU and DCC are very toxic compounds;

3. It can be removed after coupling reaction by simple washing with water. Known coupling agents and their reaction products often contaminate the product of coupling during isolation procedures and complicated purification processes are necessary;

4. It reacts at very mild conditions with high yield;

5. It has affordable price;

6. It is a stable product with easy handling and dosing is well soluble in common organic solvents, e.g. in ethyl acetate and/or in acetonitrile.

To illustrate the advantages of the coupling agent (8A) in a process of making bortezomib, the present inventors performed a comparative study vis-a-vis the known coupling agents. The results of yields, purity and reaction conditions are summarized in the Example 1 below.

The present invention deals with two processes of making bortezomib starting from a compound of general formula (2A), wherein PR is a chiral protective group. As indicated above, the useful protective group is a chiral (S)-pinanediol group and the corresponding starting protected boronic acid has thus preferably the structure corresponding to the formula (2). While the processes of the present invention will be further illustrated and exemplified on the compounds bearing chiral (S)-pinanediol protective group, the invention is not limited thereto. In an example, the other chiral protective groups in compounds of the general formula (2A) may be, e.g., chiral 1,2-dicyclohexylethane-1,2-diol (DICHED), chiral 1,2-diisopropylethane-1,2-diol (DIPED) etc.

In an illustrative example of the first process of the present invention, the compound of formula (2) reacts with the compound of formula (6), wherein R1 is hydrogen, under presence of the coupling agent of formula (8A). The formed B—OH protected compound (4) is then deprotected to bortezomib.

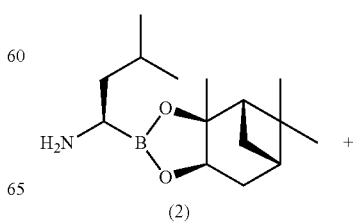

(2)

-continued

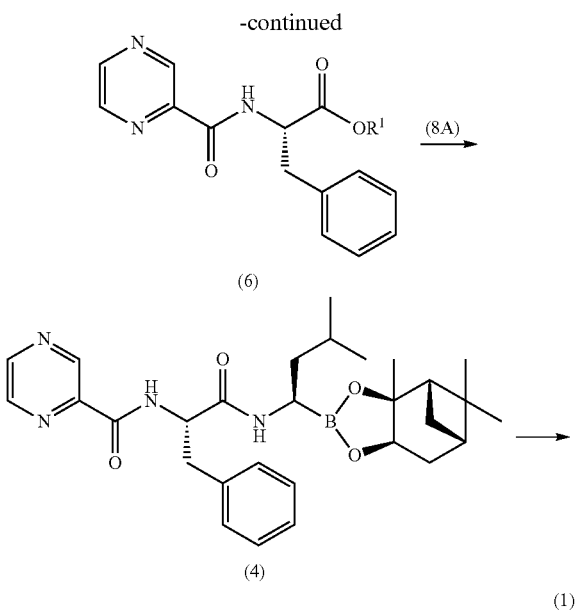

The compound of formula (2) is a known compound. It may be prepared by processes known in the art, which generally start from (S)-pinanediol and 2-methylpropane boronic acid. The processes are disclosed, e.g., in WO 2005/097809, WO 2009/004350 and WO 2009/036281. The compound (2) may be used per se or, preferably, as an acid addition salt. The most preferred acid addition salt is a trifluoroacetate salt as it is easily preparable and is crystalline.

The second reaction partner, the compound of formula (6), is advantageously prepared by a process, in which L-phenylalanine alkylester and/or its acid addition salt having the formula (5)

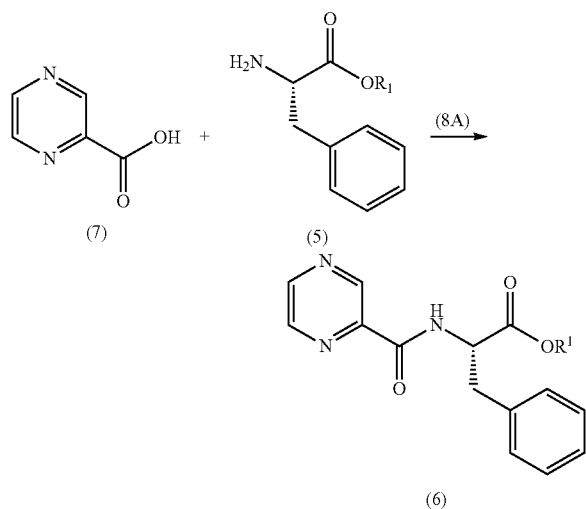

wherein R1 is a C1-C4 alkyl group and is preferably methyl group, is coupled in an inert solvent with pyrazine-2-carboxylic acid of formula (7) in the presence of a base. According to one aspect of the present invention, the coupling reaction proceeds in a presence of the coupling agent of the formula (8) above, typically with the n-propylphosphonic anhydride of the formula (8A). In an advantageous embodiment, the inert solvent may be an aliphatic, cyclic or aromatic C5-C10 hydrocarbon or a halogenated C1-C4 aliphatic hydrocarbon. The base is advantageously a tertiary amine, e.g. N-methylmorpholine. The reaction temperature is typically from −20 to 0° C., under which temperature the reaction time is about 2-4 hours. The amount of the coupling agent of formula (8) is advantageously from 1 to 2 molar equivalents in respect to the compound (5). The reaction progress may be monitored by a suitable analytical technique, e.g. by HPLC or GC. After the reaction has been terminated, the reaction mixture is elaborated by an extraction with water, by which rests of the coupling agent and the base are removed. The reaction product may be isolated from the organic phase by common means, e.g. by evaporation, or the organic phase may be used in the next step directly.

In the next step, the so formed intermediate of formula (6), in which R1 is a C1-C4 alkyl group, and is preferably methyl group, is hydrolysed by water to the compound of formula (6), in which R1 is hydrogen. Preferably, the hydrolysis is performed in a water miscible solvent in a presence of a base, e.g. an amine base. It is important to assure that essentially no epimerization occurs during the hydrolysis. Therefore, the conditions of hydrolysis must be very mild. In an advantageous mode, the basic hydrolysis under mild conditions may be performed in presence in lithium salts, for instance lithium chloride, lithium bromide, lithium nitrate, lithium trifluoroacetate, lithium tetrafluoroborate etc.

The hydrolysed compound is advantageously isolated from the reaction mixture after neutralization thereof, preferably by an extraction. The crude product may be precipitated in solid form from the extract, e.g. by using antisolvent, which typically is an aliphatic hydrocarbon such as hexane or heptanes. The crude solid may be isolated by filtration and optionally recrystallized from a suitable solvent or a solvent/antisolvent mixture.

Having the compound (2) and compound (6) available, the key step in making bortezomib according to process of the present invention comprises coupling, under presence of a base, the compound (6), in which R1 is hydrogen, with the compound (2), which preferably is charged as an acid addition salt and most preferably as trifluoroacetate salt, in an inert solvent, whereby the coupling agent necessary for the mutual reaction is the compound of formula (8), preferably of formula (8A). In an advantageous embodiment, the inert solvent may be an aliphatic, cyclic or aromatic C5-C10 hydrocarbon or a halogenated C1-C4 aliphatic hydrocarbon. The base is advantageously a tertiary amine, e.g. N-methylmorpholine. The reaction temperature is typically from −30 to 0° C., preferably from −20 to −10° C., under which temperature the reaction time is about 1-2 hours. The amount of the coupling agent of formula (8) is advantageously from 1 to 2 molar equivalents in respect to the compound (2). The reaction progress may be monitored by a suitable analytical technique, e.g. by HPLC or GC. After the reaction has been terminated, the reaction mixture is elaborated by an extraction with water, by which rests of the coupling agent and the base are removed. The reaction product may be isolated from the organic phase by common means, e.g. by evaporation and may be optionally purified, e.g. by column chromatography.

Whenever useful, reaction products of any of the steps of the process may be used in the next step without isolation from the reaction mixture.

In the last step, the so formed protected bortezomib intermediate of the formula (4) is deprotected by yielding bortezomib of formula (1). Any of deprotecting procedures known in the art may be used. In particular, the transesterification step disclosed in WO 2005/097809, in which the protected bortezomib reacts with an organic boronic acid acceptor in acidic conditions, represents an useful deprotecting process.

In an illustrative example of the second process of the present invention, the compound of formula (2) reacts in the first step with the L-phenylalanine compound of formula (5a), wherein R is a nitrogen protective group. The useful nitrogen protective group is a tert.butyloxycarbonyl group (tBOC), but is should be understood that other suitable nitrogen protective groups may be used as well.

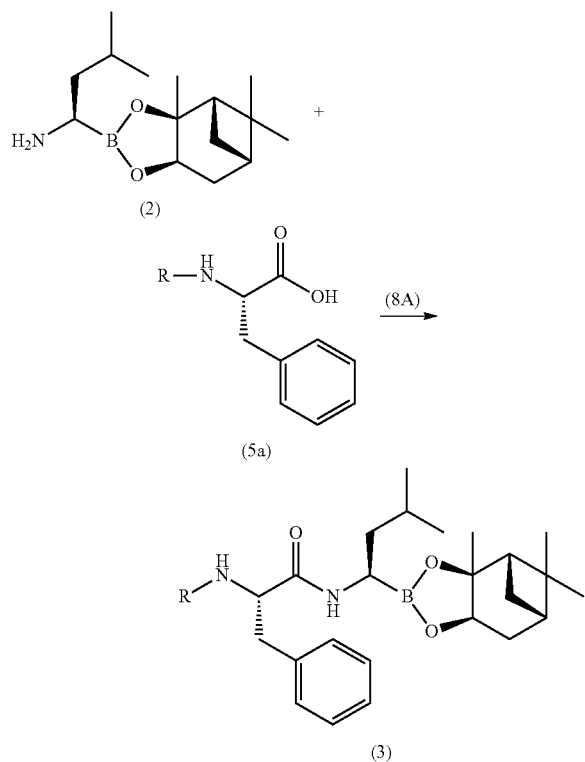

Similarly as in the first process of the present invention, the compound of formula (2) may be charged in the reaction as an acid addition salt, preferably the trifluoroacetate salt. The coupling reaction with the tBOC-protected compound (5a) typically proceeds in an inert solvent, in the presence of base and is, in accordance with the present invention, mediated by the action of the coupling agent of the formula (8), preferably (8A). The inert solvent is advantageously a chlorinated C1-C4 hydrocarbon or C5-C10 aliphatic, cyclic or aromatic hydrocarbon, the base is preferably a tertiary amine. The reaction conditions and workup of the reaction mixture are essentially the same as disclosed in the first process of the present invention.

In a next step, the protective group R in the so formed compound (3) is removed to yield a compound of formula (3) in which R is hydrogen. In case of the tBOC protective group, the deprotection is typically performed by treating the substrate with HCl in ethyl acetate. After termination of the reaction, the product may be isolated from the reaction mixture by diluting with a hydrocarbon, e.g. with heptanes, and precipitating the product as a hydrochloride salt.

In the second coupling step, the compound (3), in which R is hydrogen, reacts with the 2-pyrazinecarboxylic acid of formula (7) in the presence of the coupling agent of the formula (8), preferably (8a), in an inert solvent and in the presence of a base.

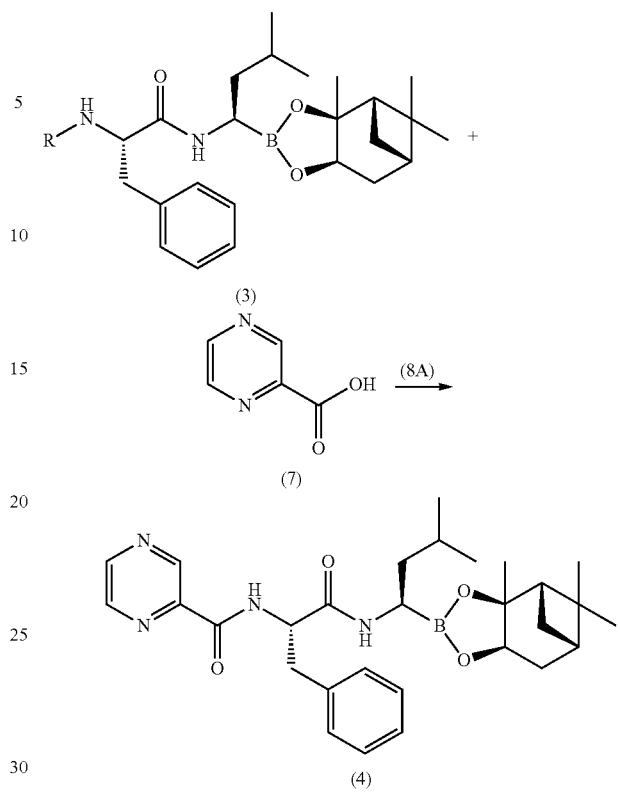

The inert solvent is advantageously a chlorinated C1-C4 hydrocarbon or C5-C10 aliphatic, cyclic or aromatic hydrocarbon, the base is preferably a tertiary amine. The reaction conditions and workup of the reaction mixture are essentially the same as disclosed in the first process of the present invention.

Whenever useful, reaction products of any of the steps of the process may be used in the next step without isolation from the reaction mixture.

In the last step, the so formed protected bortezomib of the formula (4) is deprotected yielding bortezomib of formula (1). Any of deprotecting procedures known in the art may be used. In particular, the transesterification step disclosed in WO 2005/097809, in which the protected bortezomib reacts with an organic boronic acid acceptor in acidic conditions, represents an useful deprotecting process.

The bortezomib prepared by any of the processes of the present invention and/or by obvious alternatives thereof, may be isolated in solid state in the boroxine trimeric form by a suitable precipitation process known in the art and purified if desirable to the pharmaceutical degree of purity.

The present invention is illustrated by following non-limiting examples.

EXAMPLES

Example 1

(S)-Methyl 3-phenyl-2-(pyrazine-2-carboxamido) propanoate=compound of formula (6) [$R^1$ is a methyl group]

Dissolve 2,4,6-triprop-1-yl-1,3,5-trioxa-2,4,6-triphosphinane-2,4,6-trioxide (compound of formula (8A))(192 g of 50% solution in acetonitrile, 301 mmol) in 282 ml of dichloromethane at 20-25° C. and add pyrazine 2-carboxylic acid (compound of formula (7)) (25 g, 201 mmol). Add L-phenylalanine methylester hydrochloride (43.7 g, 201 mmol) and cool the resulting suspension with stirring to −10 to −15° C. Add a solution of N-methylmorpholine (101 ml, 903 mmol) in 90 ml of dichloromethane to the pre-cooled mixture over 1 hour while keeping the reaction temperature in the range from −10 to −15° C. Stir the reaction mixture at −10 to −15° C. for 4 hours. Then pour the reaction mixture into 200 ml of water. Separate the layers and extract the aqueous layer with 2×40 ml of dichloromethane. Dry the combined organic extract over anhydrous magnesium sulphate. Evaporate volatiles (20 mbar, 45° C.). Yellow oily product is obtained (65.87 g)

Comparison of the effectivity of the compound of formula (8A) [hereinunder denoted as T3P] with commonly used coupling reagents in the synthesis of the compound of formula (6) [$R^1$ is a methyl group]:

| Coupling reagent | Compound (6) crude | | | |
|---|---|---|---|---|
| | Purity (HPLC, IN (%)) | | Reaction time (h)/ | |
| | Chemical | Chiral* | temperature (° C.) | Yield (%) |
| DCC | 61.83 | 99.9 | 0.9/0 | 76 |
| TBTU | 97.50 | 99.9 | 2.3/0 | 40 |
| DCC/HOBT | 72.63 | 99.0 | 3.5/0 | quant |
| T3P | 99.05 | 99.0 | 3.75/−10 | quant |

*Chiral purity determined as a ratio between the both enantiomers

Example 2

(S)-3-phenyl-2-(pyrazine-2-carboxamido)propanoic acid=Compound of formula (6) [$R^1$ is hydrogen]

Dissolve (S)-Methyl 3-phenyl-2-(pyrazine-2-carboxamido)propanoate (57.65 g) in 572 ml of acetonitrile and add 11.7 ml water and 84 ml of triethylamine. Cool the reaction mixture to 0° C. on ice bath and add 175.0 g of LiBr in several portions at vigorous stirring. After 10 minutes of stirring, increase the temperature to ambient temperature. (NB. A HPLC sample showed 99.97% conversion with 98.78% content of the desired product).

After 5 hours of stirring, dilute the reaction mixture with 572 ml of water and adjust pH of the solution to 3-4 (pH-paper) at 0-2° C. with approx. 56 ml of 36% HCl. Extract the solution with 3×250 ml of ethyl acetate. Dry the combined organic layers with $MgSO_4$ and concentrate them at 50° C. to 170 ml volume. Cool the formed suspension to ambient temperature and dilute with 170 ml of n-heptane. Allow to stand overnight at −10° C. Isolate crude product by filtration and wash with 2×40 ml of ethyl acetate-n-heptane mixture 1:1 (v/v).

Yield: 56.85 g of the title product as off-white crystals. HPLC: Chemical purity 98.98% (IN), Chiral purity 99.51% (IN)

Example 3

Compound of Formula (4)

Mix the (S)-3-phenyl-2-(pyrazine-2-carboxamido)propanoic acid (10.85 g, 40.0 mmol) with the trifluoroacetate salt of the compound of formula (2) (16.27 g, 40.0 mmol) in 215 ml of anhydrous dichloromethane at 20-25° C. Cool the formed white suspension under stirring to −15° C. and add N-methylmorpholine (17.7 ml, 160 mmol) while keeping the internal temperature at −10° C. Add the T3P reagent (2,4,6-triprop-1-yl-1,3,5-trioxa-2,4,6-triphosphinane-2,4,6-trioxide, 38.2 g of 50% solution in acetonitrile, 60 mmol) at the same temperature. Stir the reaction mixture at −10 to −15° C. for 1.5 hours.

Warm the reaction mixture to 20-25° C. and add 215 ml of water. Separate the layers and was the organic layer with 210 ml of brine. Dry the organic extract with anhydrous sodium sulphate and evaporate the volatiles (5 mbar, 40° C.) to an oily residue. Transfer the residue to silic gel pad (54.3 g, Silica gel 60 Merck, 40-63 µm, 230-400 Mesh) and elute crude product with a mixture of n-heptane/MTBE (460 ml). Evaporate volatiles (5 mbar, 40° C.) and yield 18.12 g of a yellow residue (86%).

HPLC: Chemical purity 98.69% (IN), Chiral purity 99.7%.

The invention having been described, it will be readily apparent to those skilled in the art that further changes and modifications in actual implementation of the concepts and embodiments described herein can easily be made or may be learned by practice of the invention, without departing from the scope of the invention as defined by the following claims.

The invention claimed is:

1. In a process for making bortezomib of formula (1),

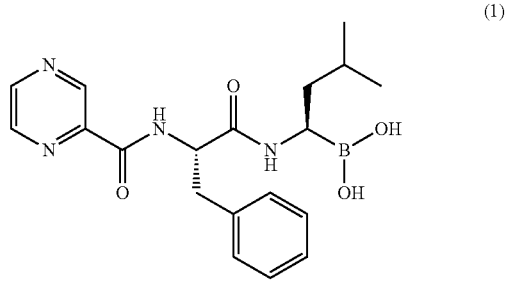 [SMILES: CC(C)C[C@H](NC(=O)[C@H](Cc1ccccc1)NC(=O)c1cnccn1)B(O)O]

or enantiomers thereof, that comprises a coupling reaction between a carboxylic acid and an amine in the presence of a coupling reagent to form one of the peptide bonds in the bortezomib structure, the improvement for which comprises that said coupling reagent comprises a cyclic alkyltriphosphonate anhydride of formula (8)

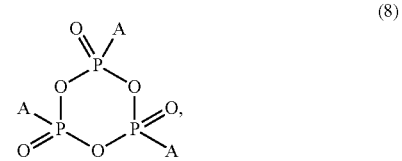

wherein A is C1-C6 alkyl group.

2. The process according to claim 1, wherein said coupling reaction produces a protected bortezomib of formula (4A), (4A)

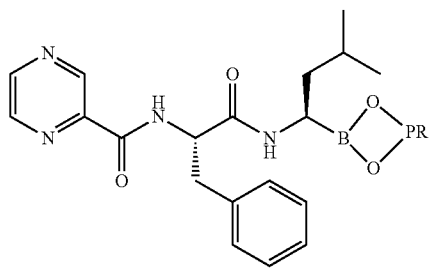

wherein PR is a chiral protective group, and which further comprises deprotecting said compound of formula (4A) to form bortezomib of formula (I) or enantiomers thereof.

3. The process according to claim 2, wherein said coupling reaction comprises coupling protected (R)-1-amino-3-methylbutylboronic acid of formula (2A), (2A)

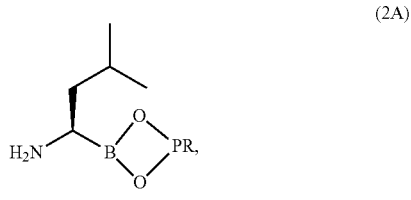

wherein PR is a chiral protective group,
with a compound of formula (6)

(6)

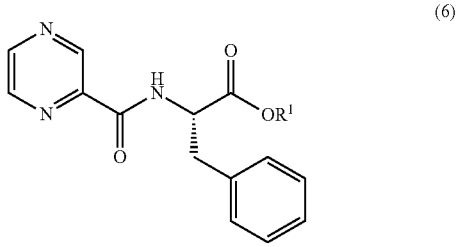

wherein R1 is hydrogen, to form said compound of formula (4A).

4. The process according to claim 3, wherein PR is an (S)-pinanediol protective group.

5. The process according to claim 2, wherein said coupling reaction comprises coupling a compound of formula (3A)

(3A)

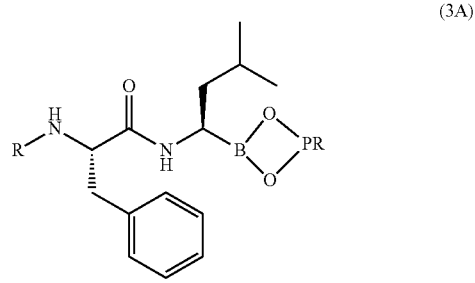

wherein R is hydrogen and PR is a chiral protective group, with a compound of formula (7), (7)

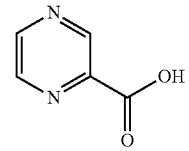

to form said compound of formula (4A).

6. The process according to claim 1, wherein said coupling reaction comprises coupling a compound of formula (5) and/or an acid addition salt thereof (5)

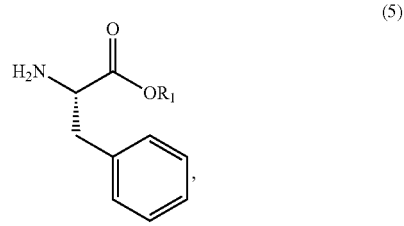

wherein R1 is C1-C4 alkyl group,
with a compound of formula (7)

(7)

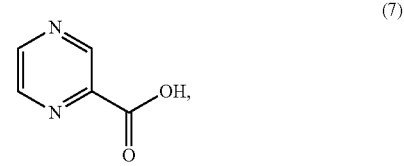

to form the bortezomib intermediate of formula (6)

(6)

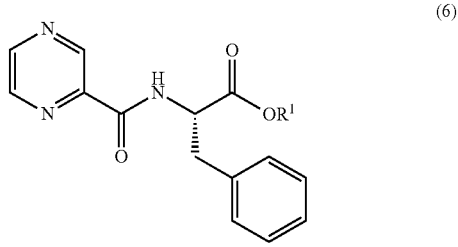

wherein R1 is C1-C4 alkyl group.

7. The process according to claim 1, wherein said coupling reaction comprises coupling a compound of formula (2A),

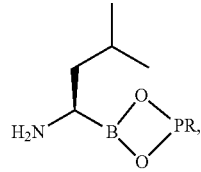

(2A)

wherein PR is a chiral protective group, with a compound of formula (5A),

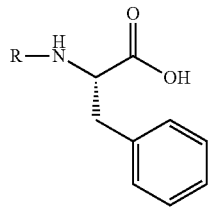

(5a)

wherein R is a N-protective group, to form the bortezomib intermediate of formula (3A)

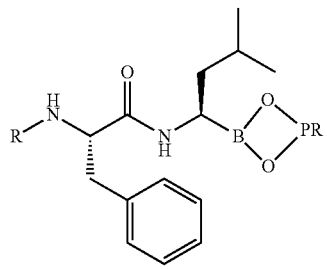

(3A)

wherein R is the N-protective group.

8. The process according to claim 7, wherein PR is an (S)-pinanediol protective group.

9. The process according to claim 1, wherein A in formula (8) is n-propyl.

10. The process according to claim 1, wherein said process for making bortezomib comprises two coupling reactions, each between a carboxylic acid and an amine in the presence of a coupling reagent, to form the two peptide bonds in the bortezomib structure, and wherein said coupling reagent in both of said coupling reactions is a compound of formula (8).

11. The process according to claim 4, wherein A in formula (8) is n-propyl.

12. The process according to claim 8, wherein A in formula (8) is n-propyl.

13. The process according to claim 10, wherein A in formula (8) is n-propyl.

* * * * *